United States Patent
Hofmann

(10) Patent No.: US 10,779,790 B2
(45) Date of Patent: Sep. 22, 2020

(54) PROVISION OF A MEDICAL IMAGE DATA SET OF A PATIENT BY MEANS OF AN X-RAY TUBE OF A COMPUTED TOMOGRAPHY SYSTEM

(71) Applicant: Siemens Healthcare GmbH, Erlangen (DE)

(72) Inventor: Christian Hofmann, Erlangen (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 0 days.

(21) Appl. No.: 16/597,272

(22) Filed: Oct. 9, 2019

(65) Prior Publication Data
US 2020/0121274 A1    Apr. 23, 2020

(30) Foreign Application Priority Data
Oct. 18, 2018    (DE) .......................... 10 2018 217 886

(51) Int. Cl.
*A61B 6/00*    (2006.01)
*A61B 6/03*    (2006.01)

(52) U.S. Cl.
CPC .............. *A61B 6/541* (2013.01); *A61B 6/032* (2013.01); *A61B 6/5205* (2013.01); *A61B 6/5217* (2013.01)

(58) Field of Classification Search
None
See application file for complete search history.

(56) References Cited

U.S. PATENT DOCUMENTS

2008/0144765 A1* 6/2008 Flohr ..................... A61B 6/503
                                                   378/9
2008/0198965 A1* 8/2008 Popescu ................ A61B 6/488
                                                   378/19
(Continued)

FOREIGN PATENT DOCUMENTS

DE    102007050889 A1    5/2009
DE    102008034564 A1    2/2010
(Continued)

OTHER PUBLICATIONS

Extended European Search Report dated Mar. 11, 2020.
Extended German Office Action for DE Application No. 102018217886, dated Aug. 21, 2019.

*Primary Examiner* — Hoon K Song
(74) *Attorney, Agent, or Firm* — Harness, Dickey & Pierce, P.L.C.

(57) ABSTRACT

A method includes determining multiple X-ray tube current profiles of the X-ray tube, satisfying a loading limit of the X-ray tube; collecting first raw data of a patient according to the first X-ray tube current profile, with at least one X-ray tube current profile parameter of the first X-ray tube current profile being adapted according to a functional parameter; adapting the second X-ray tube current profile in the control unit such that, as a function of the at least one adapted X-ray tube current profile parameter, the second X-ray tube current profile satisfies the loading limit of the X-ray tube; collecting the second raw data of the patient according to the second X-ray tube current; reconstructing the medical image data set of the imaging measurement based upon the first raw data and the second raw data. Finally, the method includes provisioning the medical image data set.

20 Claims, 3 Drawing Sheets

(56) References Cited

U.S. PATENT DOCUMENTS

2010/0027736 A1    2/2010  Bruder et al.
2017/0344701 A1   11/2017  Allmendinger
2019/0231224 A1*   8/2019  Rupcich ................ A61B 6/545

FOREIGN PATENT DOCUMENTS

DE    102012105678 A1    1/2013
DE    102016209032 B3    9/2017

\* cited by examiner

PROVISION OF A MEDICAL IMAGE DATA SET OF A PATIENT BY MEANS OF AN X-RAY TUBE OF A COMPUTED TOMOGRAPHY SYSTEM

PRIORITY STATEMENT

The present application hereby claims priority under 35 U.S.C. § 119 to German patent application number DE 102018217886.0 filed Oct. 18, 2018, the entire contents of which are hereby incorporated herein by reference.

FIELD

Embodiments of the invention generally relate to a method for provision of a medical image data set of a patient via an X-ray tube of a computed tomography system, the computed tomography system and a corresponding computer program product.

BACKGROUND

A measurement time of an imaging measurement can vary, depending on a clinical objective. Alternatively or in addition, a patient can influence the measurement time of the imaging measurement if for example a functional parameter of the patient is used in controlling the imaging measurement. Particularly if an interventional procedure takes place on the patient during the imaging measurement, the measurement time of the imaging measurement is typically not certain before the imaging measurement is performed, but can vary.

The imaging measurement is typically performed in accordance with a measurement protocol which in particular has multiple X-ray tube current profiles to be worked through in succession. The measurement time typically depends on a loading of an X-ray tube according to the multiple X-ray tube current profiles during the imaging measurement.

In order that the loading during imaging measurement preferably satisfies a loading limit of the X-ray tube, a conservative estimate of the loading is normally made before the imaging measurement is performed, as a result of which the measurement time of the imaging measurement is typically prolonged compared to a measurement time-optimized estimate. This is because a conservative estimate typically includes longer idle periods for the X-ray tubes during imaging measurement than a typical patient and/or the clinical objective normally require, it being possible to adapt the measurement protocol and thus typically to prolong the measurement time.

The idle periods can for example take into consideration a functional reference parameter of the typical patient that is for example made up of several previous imaging measurements. Idle times can in principle be chosen so as to be sufficiently generous for the loading limit of the X-ray tube to be satisfied, preferably in most cases and particularly advantageously always, during imaging measurement. The conservative estimate preferably enables planning of imaging measurement through specification of the measurement time before the imaging measurement is performed because possible variations, in particular that depend on the patient, are taken into consideration a priori. In such cases loading reserves of the X-ray tube that can prolong the measurement time are normally factored in.

SUMMARY

At least one embodiment of the invention is directed to a method for provision of a medical image data set of a patient via an X-ray tube of a computed tomography system, a corresponding computed tomography system and a corresponding computer program product by which imaging measurement can be performed flexibly.

Advantageous embodiments are described in the claims.

The method according to an embodiment of the invention is for provision of a medical image data set of a patient via an X-ray tube of a computed tomography system, the method comprising:

Determination of multiple X-ray tube current profiles of the X-ray tube in a control unit of the computed tomography system, with the multiple X-ray tube current profiles comprising a first X-ray tube current profile and a second X-ray tube current profile, forming a measurement protocol for imaging measurement in the computed tomography system and satisfying a loading limit of the X-ray tube while taking into consideration a functional reference parameter, Collection of first raw data of the patient according to the first X-ray tube current profile via the X-ray tube, with a functional parameter of the patient being recorded and with at least one X-ray tube current profile parameter of the first X-ray tube current profile being adapted during the collection of the first raw data according to the functional parameter, Adaptation of the second X-ray tube current profile in the control unit in such a way that, as a function of the at least one adapted X-ray tube current profile parameter, the second X-ray tube current profile satisfies the loading limit of the X-ray tube, Collection via the X-ray tube of second raw data of the patient according to the second adapted X-ray tube current profile, Reconstruction of the medical image data set of the imaging measurement on the basis of the first raw data and the second raw data and Provision of the medical image data set of the patient.

The method according to an embodiment of the invention is directed to a method for provision of a medical image data set of a patient via an X-ray tube of a computed tomography system, the method comprising:

determining multiple X-ray tube current profiles of the X-ray tube in a control unit of the computed tomography system, wherein the multiple X-ray tube current profiles comprise a first X-ray tube current profile and a second X-ray tube current profile, form a measurement protocol for imaging measurement in the computed tomography system and satisfy a loading limit of the X-ray tube, while taking into consideration a functional reference parameter;

collecting, via the X-ray tube, first raw data of the patient according to the first X-ray tube current profile, wherein a functional parameter of the patient is recorded and wherein at least one X-ray tube current profile parameter of the first X-ray tube current profile is adapted during the collecting of the first raw data according to the functional parameter, to create at least one adapted X-ray tube current profile parameter;

adapting the second X-ray tube current profile in the control unit such that, as a function of the at least one adapted X-ray tube current profile parameter, the second X-ray tube current profile satisfies the loading limit of the X-ray tube, to create an adapted second X-ray tube current profile;

collecting, via the X-ray tube, second raw data of the patient according to the adapted second X-ray tube current profile;

reconstructing the medical image data set of the imaging measurement based upon the first raw data and the second raw data, to create a reconstructed medical image data set; and provisioning the reconstructed medical image data set.

The computed tomography system in an embodiment has the control unit and the X-ray tube and is configured in accordance with an embodiment of the method for provision of the medical image data set via the X-ray tube.

The computed tomography system according to an embodiment of the invention is directed to a computed tomography system, comprising:

a control unit to determine multiple X-ray tube current profiles of an X-ray tube, wherein the multiple X-ray tube current profiles include a first X-ray tube current profile and a second X-ray tube current profile, form a measurement protocol for imaging measurement in the computed tomography system and satisfy a loading limit of the X-ray tube, while taking into consideration a functional reference parameter; and the X-ray tube configured to collect first raw data of the patient according to the first X-ray tube current profile, wherein a functional parameter of the patient is recorded and wherein at least one X-ray tube current profile parameter of the first X-ray tube current profile is adapted during the collecting of the first raw data according to the functional parameter, to create at least one adapted X-ray tube current profile parameter, wherein the control unit is further configured to adapt the second X-ray tube current profile in the control unit such that, as a function of the at least one adapted X-ray tube current profile parameter, the second X-ray tube current profile satisfies the loading limit of the X-ray tube, to create an adapted second X-ray tube current profile, the X-ray tube being further configured to collect second raw data of the patient according to the adapted second X-ray tube current profile, reconstruct the medical image data set of the imaging measurement based upon the first raw data and the second raw data, to create a reconstructed medical image data set, and provision the reconstructed medical image data set.

A non-transitory computer readable medium according to an embodiment of the invention is directed to a non-transitory computer readable medium storing a program that is directly loadable onto a memory of a processing unit, the program including program code segments to execute an embodiment of the method of the present application when the computer program is executed in the processing unit.

A computer program product in an embodiment that is directly loadable onto a memory of the processing unit has program code segments/modules in order to execute an embodiment of the method for provision of the medical image data set by way of the X-ray tube of the computed tomography system when the computer program product is executed in the processing unit. The memory can have the storage unit and/or the main memory.

The computer program product is for example stored on a physical, machine-readable medium and/or digitally recorded as a data package on a computer network. The computer program product can constitute the physical, machine-readable medium and/or the data package on the computer network. An embodiment of the invention can thus relate both to the physical, machine-readable medium and/or the data package on the computer network.

BRIEF DESCRIPTION OF THE DRAWINGS

The invention is described in more detail and explained below with reference to the example embodiments shown in the figures. As a basic principle in the following description figures, structures and units that remain essentially the same are referred to with the same reference characters as on their respective first appearances in the text.

In the figures.

DETAILED DESCRIPTION OF THE EXAMPLE EMBODIMENTS

Figure 1:
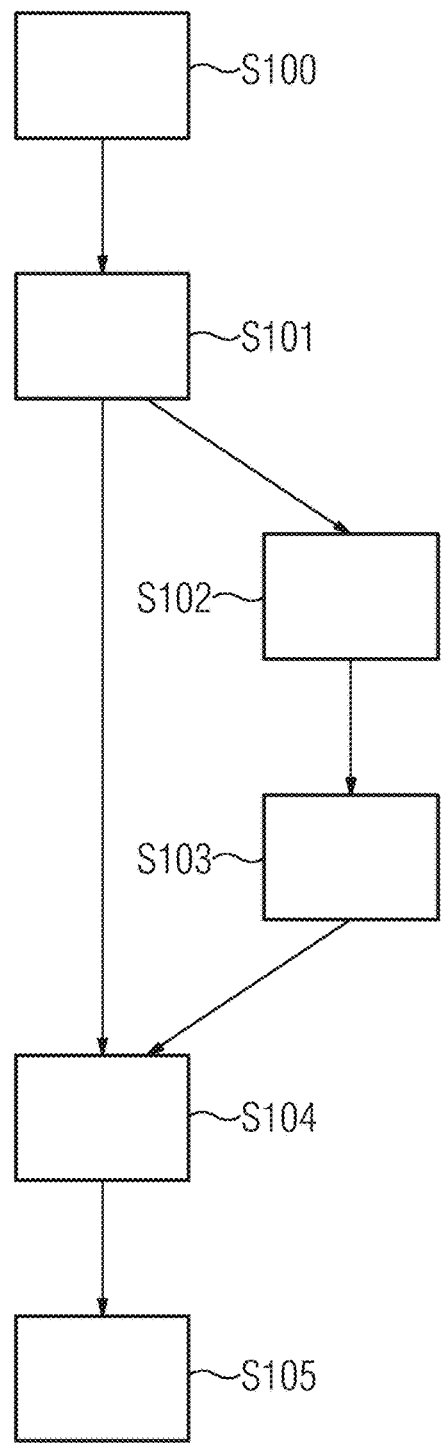
FIG. 1 shows a method for provision of a medical image data set of a patient via an X-ray tube of a computed tomography system in a first example embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to an embodiment of the invention is for provision of a medical image data set of a patient via an X-ray tube of a computed tomography system, the method comprising:

Determination of multiple X-ray tube current profiles of the X-ray tube in a control unit of the computed tomography system, with the multiple X-ray tube current profiles comprising a first X-ray tube current profile and a second X-ray tube current profile, forming a measurement protocol for imaging measurement in the computed tomography system and satisfying a loading limit of the X-ray tube while taking into consideration a functional reference parameter, Collection of first raw data of the patient according to the first X-ray tube current profile via the X-ray tube, with a functional parameter of the patient being recorded and with at least one X-ray tube current profile parameter of the first X-ray tube current profile being adapted during the collection of the first raw data according to the functional parameter, Adaptation of the second X-ray tube current profile in the control unit in such a way that, as a function of the at least one adapted X-ray tube current profile parameter, the second X-ray tube current profile satisfies the loading limit of the X-ray tube, Collection via the X-ray tube of second raw data of the patient according to the second adapted X-ray tube current profile, Reconstruction of the medical image data set of the imaging measurement on the basis of the first raw data and the second raw data and Provision of the medical image data set of the patient.

The method offers the following advantages in particular:

A flexible performance of the imaging measurement is made possible by using the at least one adapted X-ray tube current profile parameter for adapting the second X-ray tube current profile. The method therefore in particular enables adaptation of the measurement protocol, in particular of the X-ray tube current profiles, depending on the patient, preferably during imaging measurement. The measurement protocol, particularly the X-ray tube current profiles thereof, can be advantageously adapted during imaging measurement. The quality of the first raw data and/or of the second raw data, in particular the image quality of the medical image data set, can be advantageously raised through flexible performance of imaging measurement.

A measurement time of the imaging measurement is preferably reduced because flexible performance makes a conservative estimate, which typically factors in longer idle periods than a measurement time-optimized estimate, superfluous and/or is corrected during imaging measurement analogously to the measurement time-optimized estimate. If the measurement time of the imaging measurement is reduced, the cost of performing the imaging measurement is normally reduced. Alternatively or in addition, patient comfort can be increased.

Provision of the medical image data set of the patient via the X-ray tube of the computed tomography system can then be faster, in particular, if the patient breathes more regularly than a typical patient with the functional reference parameter. Preferably, performance of the imaging measurement can be represented by the measurement time-optimized estimate, rather than by the conservative estimate.

The medical image data set can for example correspond to a functional volumetric image data set. The medical image data set can for example have a first medical image corresponding to the first raw data and a second medical image corresponding to the second raw data. The medical image data set can in particular be available in a DICOM image format.

If for example a clinical objective is related to a cardiac examination of the patient it is preferably possible for the medical image data set to be used for the cardiac examination. In other words, no further medical image data set is typically provided for the clinical objective because the medical image data set can typically be equivalent to the functional volumetric image data set. The clinical objective can in particular be related to an examination of a physiological function of the patient, for example a cardiac examination and/or a respiratory examination. It is in principle conceivable that following the provision of the medical image data set related to a first clinical objective the next medical image data set is provided in relation to a second clinical objective.

An X-ray tube current profile of the X-ray tube generally includes at least one X-ray tube current profile parameter, for example an X-ray tube current duration during which X-radiation with an X-ray tube current amplitude is normally emitted by the X-ray tube. The X-ray tube current amplitude during the X-ray tube current duration can be constant or can vary. In addition, the X-ray tube current profile can include an X-ray tube idle period during which no X-radiation is typically emitted and/or the X-ray tube can cool down. Working through the X-ray tube current profile comprises in particular emission of the X-radiation with the X-ray tube current amplitude during the X-ray tube current duration. Working through the X-ray tube current profile can additionally include complying with the X-ray tube idle period. A loading of the X-ray tube normally correlates with a product of the X-ray tube current duration and the X-ray tube current amplitude. Patient dose loadings typically depend on the X-ray tube loading. The X-ray tube is loaded during the X-ray tube current duration in particular.

The multiple X-ray tube current profiles thus form the measurement protocol for the imaging measurement because the data that is collected by working through the multiple X-ray current profiles is normally the raw data that is used for the provision of the medical image data set. After the multiple X-ray tube current profiles have been worked through collection of the raw data of the medical imaging, in particular in accordance with the measurement protocol, is normally complete. Typically, the first X-ray tube current profile is worked through before the second X-ray tube current profile. The beginning of the first X-ray tube current profile and the end of the second X-ray tube current profile in particular form a measurement time of the imaging measurement. The measurement protocol typically has table incrementation, X-ray tube voltage, a measurement range, a reconstruction core and/or X-ray tube collimation in addition to the multiple X-ray tube current profiles. At least part of the measurement protocol can for example be specified and/or adapted by a user. The computed tomography system can comprise a planning unit for the specification and/or adaptation of the measurement protocol by the user. The planning unit can have a display unit and/or input unit.

The loading limit of the X-ray tube can for example be specified by a manufacturer of the X-ray tube and/or of the computed tomography system and/or be unalterable. The loading limit of the X-ray tube is preferably satisfied in such a way that the loading of the X-ray tube does not exceed and preferably satisfies the loading limit during imaging measurement, in particular during the working through of the X-ray tube current profiles. The X-ray tube is preferably operated within the normal range during imaging measurement if the loading limit of the X-ray tube is satisfied. If for example the X-ray tube is operated outside the normal range the loading of the X-ray tube can result in unplanned discontinuation of the medical imaging without provision of the medical image and/or cause increased wear of the X-ray tube and/or destruction of the X-ray tube and/or make an additional cooling phase necessary following the medical imaging. Whether or not the loading limit is being satisfied during imaging measurement can for example be determined via a sensor of the computed tomography system and communicated to the control unit, it being possible, for example when operating outside the normal range, for the control unit to discontinue the medical imaging and/or schedule the additional cooling phase, in particular any prolongation of an X-ray tube idle period. Advantageously, the life of an X-ray tube can be increased and/or maintenance costs reduced through satisfaction of the loading limit.

The control unit is preferably configured to control imaging measurement, in particular in accordance with the functional parameter of the patient. The control unit is preferably configured to determine the multiple X-ray tube current profiles of the X-ray tube in such a way that the loading limit in particular is satisfied. The control unit typically determines the multiple X-ray tube current profiles on the basis of the measurement time-optimized estimate because the second X-ray tube current profile is normally adapted if the at least one X-ray tube current profile parameter of the first X-ray tube current profile is adapted. It is in principle conceivable that the control unit determines the multiple X-ray tube current profiles on the basis of a conservative estimate. A measurement time-optimized estimate can typically be advantageous as regards the measurement time of the imaging measurement, particularly if the measurement time is reduced as a result. A conservative estimate typically takes more of the variations that can occur during medical imaging into consideration than a measurement time-optimized estimate. The X-ray tube idle period is normally longer in the case of a conservative estimate than in the case of a measurement time-optimized estimate.

For determining the multiple X-ray tube current profiles the control unit can have control program code segments/modules in which the loading limit is preferably shown. A processing unit of the computed tomography system is configured particularly to implement the control program code segments/modules. In particular, the processing unit can have a main memory and/or a processor and/or a storage unit. The loading limit can typically be retrieved from the storage unit.

The functional reference parameter is for example determined in such a way that a reference value from a textbook and/or that corresponds to a typical patient in a patient collective is defined. It is in principle conceivable that the functional reference parameter is recorded before imaging measurement, depending on the patient, and the functional parameter of the patient is recorded during imaging measurement. In such cases the functional reference parameter and the functional parameter of the patient differ from one another, particularly as regards the point in time at which they are recorded. The functional parameter of the patient can for example constitute a functional real time parameter of the patient during imaging measurement. The functional reference parameter can take a tolerance range into consideration. In particular the functional reference parameter takes into consideration the regularity and/or the amplitude and/or the frequency of the physiological function of the patient. The physiological function can in particular include the respiration of the patient and/or the cardiac phase of the patient.

Satisfying the loading limit can be equivalent to taking the loading limit into consideration. Satisfying the loading limit can include setting an aggregate loading limit for the imaging measurement that the multiple X-ray tube current profiles must satisfy. Alternatively or additionally satisfaction of the loading limit can include each X-ray tube current profile satisfying a profile loading limit. Typically the multiple X-ray tube current profiles are determined in such a way that the multiple X-ray tube current profiles satisfy the profile loading limit and the aggregate loading limit. The aggregate loading limit is for example satisfied if, as a result of the multiple X-ray tube current profiles, a sum of the loadings is smaller than or equal to the aggregate loading limit.

In addition to the functional reference parameter the loading limit can take a maximum X-ray tube current amplitude and/or a maximum X-ray tube current duration and/or a maximum loading of the X-ray tube and/or a maximum dose loading of the patient into consideration. The loading limit can depend on aggregated operating hours of the X-ray tube. The operating hours are in particular calculated from the measurement time of the imaging measurement and from measurement times of further imaging measurements. The operating hours will typically depend on X-ray tube current profiles of the X-ray tube, for example since the manufacture of the X-ray tube and/or since a servicing of the X-ray tube. Typically, the fewer the operating hours of the X-ray tube the higher the loading of the X-ray tube can be. For example the X-ray tube and/or the computed tomography system has the storage unit for storing the operating hours of the X-ray tube. When it depends on the measurement time-optimized estimate the loading limit can be lower compared to a loading limit that depends on the conservative estimate. The measurement time-optimized estimate can normally lead to higher loading of the X-ray tube than the conservative estimate. In principle, the lower the loading limit of the X-ray tube, the longer the idle period of the X-ray tube.

The measurement protocol can comprise a first functional phase and a second functional phase, with the first raw data preferably being collected during the first functional phase and the second raw data being collected during the second functional phase. The first functional phase and the second functional phase can differ from one another, preferably in a phase within a period of physiological function of the patient, with for example the first raw data being collected during an inspiration of the patient and the second raw data being collected during an expiration of the patient.

Alternatively or in addition the period of physiological function can include contrast medium addition and contrast medium washout and/or cardiac phases of a cardiac rhythm of the patient. In particular, the contrast medium addition and the contrast medium washout are contrast medium phases. The first functional phase and the second functional phase can differ from another at a z-position in a measurement range of the imaging measurement in that the first raw data is collected at a first z-position during the first functional phase and the second raw data is collected at a second z-position during the second functional phase. For example, in such cases the inspiration, particularly in a first respiratory cycle of the patient, can be recorded at the first z-position and the inspiration, particularly in a second respiratory cycle of the patient, be recorded at the second z-position, with the first respiratory cycle typically occurring before the second respiratory cycle.

In principle it is conceivable that the first functional phase and the second functional phase differ from one another in the phase within the period of physiological function of the patient and in the z-position. For example, in such cases the inspiration of the patient can be recorded at the first z-position and the expiration of the patient be recorded at the second z-position. The multiple X-ray tube current profiles can for example vary and/or be determined as a function of the z-position in the measurement range of imaging measurement and/or of the functional phase of the measurement protocol.

The control unit can typically trigger the collection of the first raw data according to the first X-ray tube current profile and/or trigger the collection of the second raw data according to the second X-ray tube current profile. The first X-ray tube current profile is normally worked through in order to collect the first raw data. The second X-ray tube current profile is normally worked through in order to collect the second raw data.

The functional parameter of the patient is typically collected during the working through of the X-ray tube current profile, preferably at a defined scanning rate. The scanning rate can for example be 1 Hz, advantageously 50 Hz and/or particularly advantageously less than 50 Hz. Advantageously the scanning rate is between 0.1 and 200 Hz, and particularly advantageously between 40 and 60 Hz.

The functional parameter can for example be recorded by way of a functional patient monitoring unit that can in particular comprise a respiration belt, a spirometer, a camera and/or an echocardiograph. The camera can in particular be a 3D camera and/or a video camera and/or an infrared camera.

The first X-ray tube current profile is typically synchronized with the functional parameter, in particular with the physiological function, of the patient, through adaptation of the at least one X-ray tube current profile parameter. The adaptation of the at least one X-ray tube current profile parameter is normally performed if the functional reference parameter and the functional parameter of the patient differ from one another, in particular as regards the regularity and/or the amplitude and/or the frequency of the physiological function of the patient. Typically, the functional reference parameter and the functional parameter of the patient can be associated with the same clinical objective.

Adaptation of the at least one X-ray tube current profile parameter comprises in particular the adaptation of the imaging measurement performed on the patient, for example on the basis of the conservative estimate and/or the measurement time-optimized estimate. The adaptation of the at least one X-ray tube current profile parameter is preferably performed at an adaptation frequency higher than 1 Hz, advantageously higher than 50 Hz and particularly advantageously higher than 200 Hz. The adaptation frequency is advantageously between 0.1 and 500 Hz, and particularly advantageously between 10 and 100 Hz. The adaptation frequency can correspond to the frequency of the functional patient monitoring unit. Depending on the adaptation frequency the control unit can preferably adapt the first X-ray tube current profile, in particular the at least one X-ray tube current profile parameter, to the functional parameter of the patient.

The adaptation of the at least one X-ray tube current profile parameter is in particular performed in such a way that an integral of the first X-ray tube current profile is increased or reduced, or remains constant, during adaptation. The integral of the first X-ray tube current profile typically corresponds to a surface that accords with the first X-ray tube current amplitude and the first X-ray tube current duration. The integral typically correlates with the loading X-ray tube. During adaptation of the at least one X-ray tube current profile parameter the loading limit of the X-ray tube is typically taken into consideration. Adaptation of the at least one X-ray tube current profile parameter can include shifting and/or changing the at least one X-ray tube current profile parameter.

The control unit can for example control the X-ray tube in such a way that the first raw data is collected during the first functional phase and before the second functional phase. For example, in order that the first raw data can be collected during the first functional phase and before the second functional phase, the at least one X-ray tube current profile parameter is adapted. The control unit can preferably determine whether the first raw data is being collected during the first functional phase and before the second functional phase. The control unit can monitor in particular determine by comparing the functional parameter with the measurement protocol, and control the collection of the first raw data in such a way that the first raw data is collected during the first functional phase and before the second functional phase.

The second X-ray tube current profile in the control unit is normally adapted after collection of the first raw data and/or before collection of the second raw data.

The adaptation of the second X-ray tube current profile can be performed in such a way that an integral of the second X-ray tube current profile is reduced or increased, or remains constant, during adaptation. If the integral of the second X-ray tube current profile remains constant, two X-ray tube current profile parameters are normally adapted, in particular in such a way that the adaptation of the two X-ray tube current profile parameters compensate for one another as regards the integral of the second X-ray tube current profile. Adaptation can include increasing, lengthening, shortening and/or reducing the second X-ray tube current profile.

The fact that, as a function of the at least one adapted X-ray tube current profile parameter, the second X-ray tube current profile satisfies the loading limit of the X-ray tube refers in particular that the at least one adapted X-ray tube current profile parameter and the loading limit of the X-ray tube are used as starting parameters for the adaptation. The adaptation of the second X-ray tube current profile parameter can be performed on the basis of the conservative estimate and/or the measurement time-optimized estimate.

In principle, the functional parameter of the patient can be collected during collection of the second raw data and at least one X-ray tube current profile parameter of the second X-ray tube current profile adapted. The control unit can for example control the X-ray tube in such a way that the second raw data can be collected after the first functional phase and during the second functional phase.

The first raw data and/or the second raw data can in particular be projection data of the computed tomography system. The first raw data and/or the second raw data can for example be stored in a radiology information system and/or in a PACS image archiving system and/or in the storage unit of the computed tomography system. The control unit can comprise a reconstruction unit for the reconstruction of the medical image data set. The control unit is typically connected to the radiology information system and/or the PACS image archiving system and/or the storage unit, particularly for calling the first raw data and/or the second raw data and/or the provision of the medical image data set. The reconstruction is performed on the basis of the reconstruction core of the measurement protocol. Reconstruction includes in particular a filtered back projection and/or an iterative reconstruction specification. The medical image data set shows in particular the measurement range, for example with the multiple z-positions and/or in the functional phase of the measurement protocol.

The medical image data set can in particular be provided on the display unit of the computed tomography system. For example the user can evaluate the clinical objective of the medical imaging by way of the medical image data set on the display unit. The medical image data set can be transferred to the radiology information system and/or the PACS image archiving system and/or the storage unit before or after being provided.

One embodiment variant provides that the functional parameter of the patient describes a respiration and/or a cardiac phase of the patient. This embodiment in particular is advantageous because the clinical objective associated with the respiratory examination and/or the cardiac examination can advantageously be evaluated by way of the medical image.

One embodiment variant provides that the measurement protocol for the collection of the first raw data and the measurement protocol for the collection of the second raw data differ from one another in at least one parameter on the following list:
  in the z-position of the measurement range of the measurement protocol,
  in the phase within the period of physiological function of the patient.

In this embodiment variant the measurement protocol typically has the first functional phase and the second functional phase. If the measurement protocols in the z-position of the measurement range differ from one another the medical image data set corresponds in particular to a volumetric image data set. If the measurement protocols differ from one another in the phase within the period of physiological function of the patient, the medical image data set corresponds in particular to a functional image data set. If the measurement protocols differ from one another in the z-position and in the phase within the period of physiological function of the patient, the medical image data set corresponds in particular to the functional volumetric image data set, which can for example be a 4D image data set.

One embodiment variant provides that the adaptation of the second X-ray tube current profile is performed using an artificial neural network. This embodiment variant is advantageous in that the artificial neural network can make better adaptation of the X-ray tube current profile possible because the artificial neural network typically is trained before the imaging measurement and/or is further educated during the imaging measurement. The artificial neural network typically has an entry layer and an exit layer that are typically connected via edges between the entry layer and the exit layer and/or via edges between at least one concealed layer between the entry layer and the exit layer. Weights of the edges are normally determined during training and/or during further education, for example on the basis of previous imaging measurements and/or on the basis of the imaging measurement.

One embodiment variant provides that the loading limit of the X-ray tube includes a temperature threshold value of the X-ray tube. The temperature threshold value describes in particular a maximum temperature of the X-ray tube. In normal operation the X-ray tube can typically be loaded up to a maximum temperature during imaging measurement. The sensor of the computed tomography system can in particular be a temperature sensor. This embodiment variant is advantageous because it prevents wear of the X-ray tube increasing, in particular increasing exponentially, as a result of the maximum temperature being exceeded and/or prevents the X-ray tube from being destroyed. This embodiment variant enables in particular longer operation of the X-ray tube.

One embodiment variant provides that the at least one X-ray tube current profile parameter comprises a first X-ray tube current amplitude and/or a first X-ray tube current duration and/or a first X-ray tube idle period. This embodiment variant advantageously comprises that the first X-ray tube current amplitude and/or the first X-ray tube current duration and/or the first X-ray tube idle period are adapted during collection of the first raw data on the basis of the functional parameter. It is in principle conceivable that when the at least one X-ray tube current profile parameter is adapted any combination of the first X-ray tube current amplitude, of the first X-ray tube current duration and of the first X-ray tube idle period is adapted. Adaptation can include increasing, lengthening, shortening and/or reducing the at least one X-ray tube current profile parameter.

One embodiment variant provides that the adaptation of the second X-ray tube current profile comprises adaptation of a second X-ray tube current amplitude and/or of a second X-ray tube current duration and/or of a second X-ray tube idle period. This embodiment advantageously specifies that when the second X-ray tube current profile is adapted only a single X-ray tube current profile parameter or multiple X-ray tube current profile parameters can be adapted.

One embodiment variant provides that a reduction in the second X-ray tube current profile occurs during adaptation, as a function of an extension of the first X-ray tube current profile as a result of the functional parameter of the patient, in order to satisfy the loading limit of the X-ray tube. Extending the first X-ray tube current profile includes in particular increasing the integral of the first X-ray tube current profile. The fact that the first X-ray tube current profile and/or the second X-ray tube current profile is reduced and/or extended as a result of the functional parameter refers in particular to the multiple X-ray tube current profiles being adapted on the basis of the functional parameter of the patient, preferably continuously during imaging measurement of the physiological function of the patient.

In this example embodiment adaptation of the first X-ray tube current profile as a result of the adaptation of the at least one X-ray tube current profile parameter is advantageously compensated for by the fact that the second X-ray tube current profile is adapted.

One embodiment variant provides that the second X-ray tube current amplitude is reduced. This embodiment variant advantageously characterizes that adaptation of the X-ray tube current profile can lead to a reduction in the dose loading of the patient.

One embodiment variant provides that the second X-ray tube current duration is reduced. In this embodiment variant the measurement time is preferably shortened.

One embodiment variant provides that a lengthening of the second X-ray tube idle period occurs as a function of an extension of the first X-ray tube current profile as a result of the functional parameter of the patient. This embodiment variant is particularly advantageous because, as a result of the second X-ray tube idle period being adapted, the dose loading of the patient remains constant throughout the second X-ray tube current profile.

One embodiment variant provides that an extension of the second X-ray tube current profile occurs during adaptation as a function of a reduction of the first X-ray tube current profile as a result of the functional parameter of the patient. This example embodiment has a particular advantage in that the loading of X-ray tube is distributed particularly so that the aggregate loading limit on the multiple X-ray tube current profiles is satisfied.

One embodiment variant provides that the second X-ray tube current amplitude and/or the second X-ray tube current duration are increased. Through increasing the integral of the second X-ray tube current profile the quality of the second raw data, in particular the image quality of the medical image data set, can be advantageously increased.

The computed tomography system has the control unit and the X-ray tube and is configured in accordance with an embodiment of the method for provision of the medical image data set via the X-ray tube.

A computer program product that is directly loadable onto a memory of the processing unit has program code segments/modules in order to execute an embodiment of the method for provision of the medical image data set by way of the X-ray tube of the computed tomography system when the computer program product is executed in the processing unit. The memory can have the storage unit and/or the main memory.

The computer program product can be a computer program or comprise a computer program. The computer program product has in particular the program code segments/modules which display the method steps according to an embodiment of the invention. As a result the method according to an embodiment of the invention can be defined and designed as reproducible, and control exercised over the disclosure of the method according to an embodiment of the invention. The computer program product is preferably configured in such a way that the processing unit can execute the method steps according to an embodiment of the invention by way of the computer program product.

The program code segments/modules can in particular be loaded onto a memory of the processing unit and typically executed by way of a processor of the processing unit with access to the memory. If the computer program product, in particular the program code segments/modules, is executed in the processing unit, all embodiment variants according to the invention of the described method can typically be performed.

The computer program product is for example stored on a physical, machine-readable medium and/or digitally recorded as a data package on a computer network. The computer program product can constitute the physical, machine-readable medium and/or the data package on the computer network. An embodiment of the invention can thus relate both to the physical, machine-readable medium and/or the data package on the computer network.

The physical, machine-readable medium is normally directly connectible to the processing unit, for example by the physical, machine-readable medium being inserted into a DVD drive or plugged into a USB port, via which the processing unit can have read/write access, in particular read access, to the physical, machine-readable medium. The data package can preferably be retrieved from the computer network. The computer network can have the processing unit or be directly connected to the processing unit via a wide area network (WAN) or a (wireless) local area network (WLAN or LAN) connection. For example the computer program product can be digitally recorded on a Cloud server at a memory location of the computer network, transferred to the processing unit via the internet by way of the WAN and/or by way of the WLAN or LAN, in particular by calling a download link that directs to the memory location of the computer program product.

Features, advantages or alternative embodiment variants mentioned in the description of the device can also be deemed to apply to the method and vice versa. In other words, claims for the method can be developed with features of the device and vice versa. In particular, the device according to an embodiment of the invention can be used in the method.

FIG. 1 shows a flow diagram of the method for provision of the medical image data set of the patient via the X-ray tube of the computed tomography system in the first example embodiment.

Method step S100 indicates a determination of multiple X-ray tube current profiles of the X-ray tube in a control unit of the computed tomography system, with the multiple X-ray tube current profiles comprising a first X-ray tube current profile and a second X-ray tube current profile, forming a measurement protocol for imaging measurement in the computed tomography system and satisfying a loading limit of the X-ray tube while taking a functional reference parameter into consideration.

Method step S101 indicates a collection of first raw data of the patient according to the first X-ray tube current profile via the X-ray tube, with a functional parameter of the patient being recorded and with at least one X-ray tube current profile parameter of the first X-ray tube current profile being adapted during the collection of the first raw data according to the functional parameter.

Method step S102 indicates an adaptation of the second X-ray tube current profile in the control unit in such a way that, as a function of the at least one adapted X-ray tube current profile parameter, the second X-ray tube current profile satisfies the loading limit of the X-ray tube.

Method step S103 indicates a collection of second raw data of the patient according to the second adapted X-ray tube current profile via the X-ray tube.

Method step S104 indicates a reconstruction of the medical image data set of the imaging measurement according to the first raw data and the second raw data.

Method step S105 indicates a provision of the medical image data set of the patient.

Figure 2:
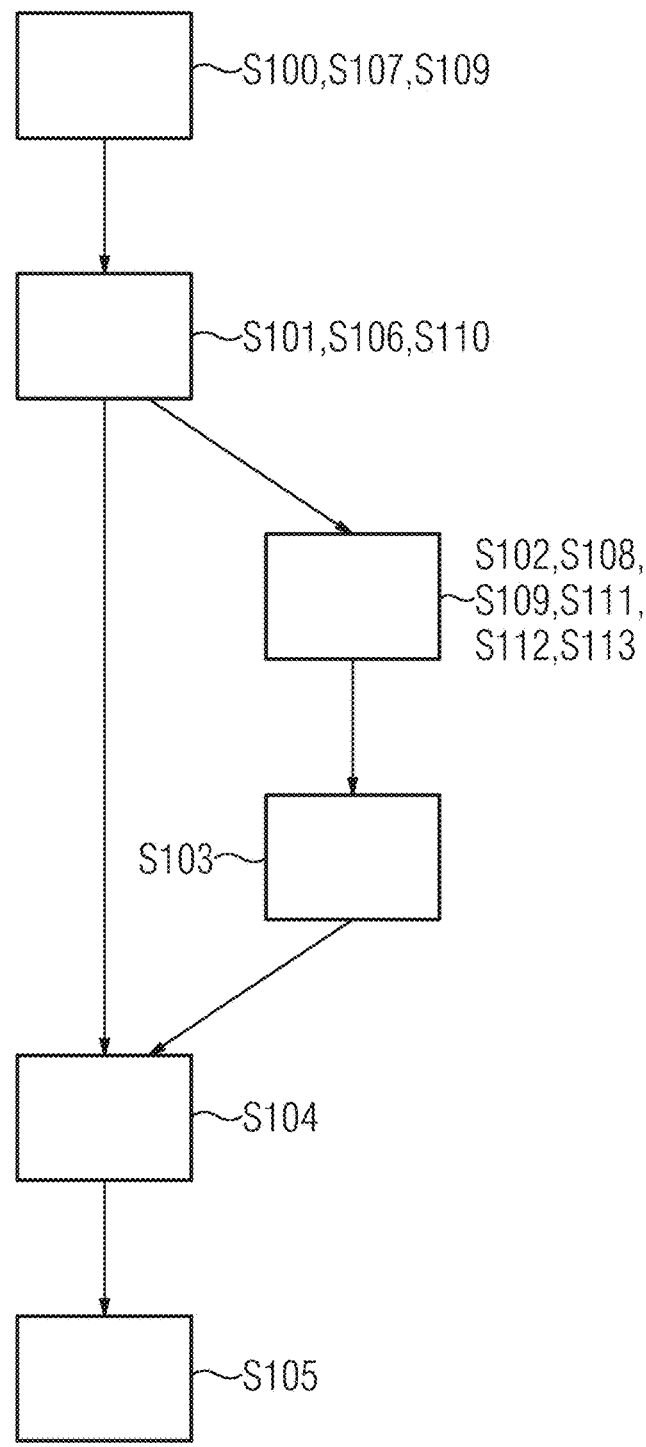
FIG. 2 shows the method in a second example embodiment.

FIG. 2 shows a flow diagram of the method in a second example embodiment.

Method step S106 indicates that the functional parameter of the patient describes a respiration and/or a cardiac phase of the patient.

Method step S107 indicates that the measurement protocol for the collection of the first raw data and the measurement protocol for the collection of the second raw data differ from one another in at least one parameter on the following list:

in a z-position of a measurement range of the measurement protocol, in a phase within the period of physiological function of the patient.

Method step S108 indicates that the adaptation of the second X-ray tube current profile is performed using an artificial neural network.

Method step S109 indicates that the loading limit of the X-ray tube includes a temperature threshold value of the X-ray tube.

Method step S110 indicates that the at least one X-ray tube current profile parameter comprises a first X-ray tube current amplitude and/or a first X-ray tube current duration and/or a first X-ray tube idle period.

Method step S111 indicates that the adaptation of the second X-ray tube current profile comprises adaptation of a second X-ray tube current amplitude and/or of a second X-ray tube current duration and/or of a second X-ray tube idle period.

Method step S112 indicates that a reduction in the second X-ray tube current profile occurs during adaptation, as a function of an extension of the first X-ray tube current profile as a result of the functional parameter of the patient, in order to satisfy the loading limit of the X-ray tube.

Method step S113 indicates that an extension of the second X-ray tube current profile occurs during adaptation as a function of a reduction of the first X-ray tube current profile as a result of the functional parameter of the patient.

Alternatively or in addition to the method steps S112 and S113 a further method step, not shown in FIG. 2, can indicate that a lengthening of the second X-ray tube idle time occurs as a function of an extension of the first X-ray tube current profile as a result of the functional parameter of the patient.

Figure 3:
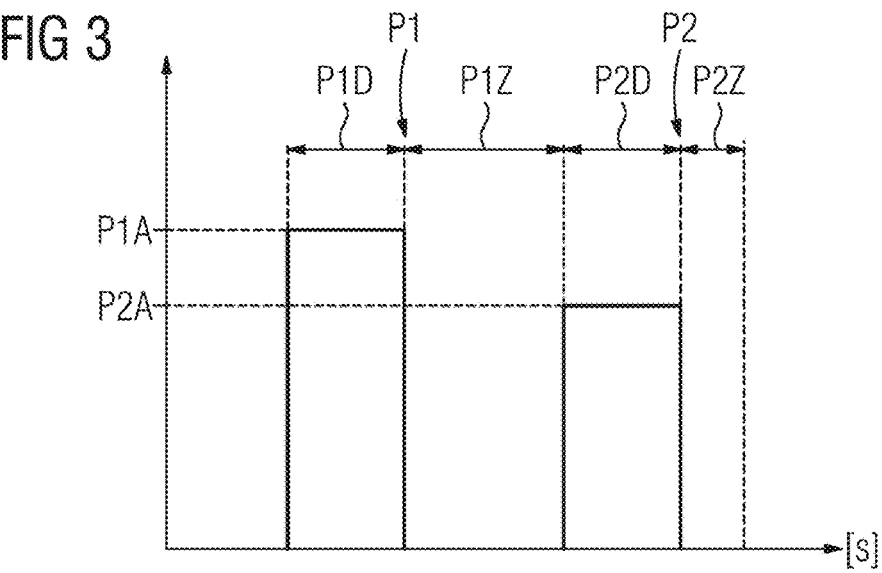
FIG. 3 is a schematic representation of the multiple X-ray tube current profiles before collection of the first raw data.
Figure 4:
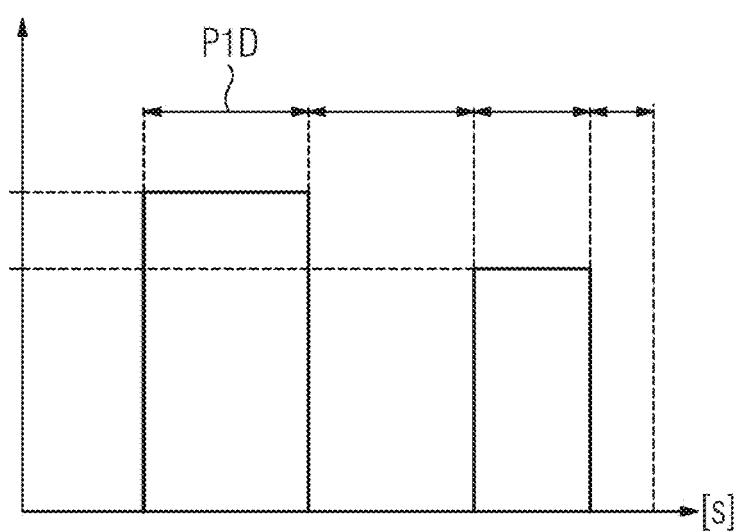
FIG. 4 is a schematic representation of the multiple X-ray tube current profiles after collection of the first raw data and before adaptation of the second X-ray tube current profile.
Figure 5:
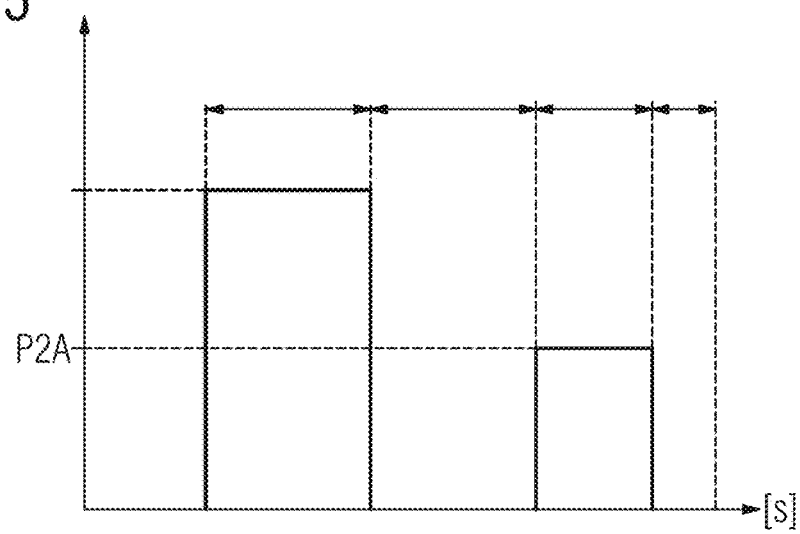
FIG. 5 is a schematic representation of the multiple X-ray tube current profiles after adaptation of the second X-ray tube current profile and FIG. 6 shows a computed tomography system.

FIG. 3, FIG. 4 and FIG. 5 show by way of example the adaptation of the at least one X-ray tube current profile parameter and of the second X-ray tube current profile.

FIG. 3 is a schematic representation of the multiple X-ray tube current profiles P1, P2 before collection of first raw data. A first X-ray tube current profile P1 includes in particular a first X-ray tube current amplitude P1A, a first X-ray tube current duration P1D and a first X-ray tube idle time P1Z. A second X-ray tube current profile P2 includes in particular a second X-ray tube current amplitude P2A, a second X-ray tube current duration P2D and a second X-ray tube idle time P2Z. For reasons of clarity, in FIG. 4 and FIG. 5 only those structures and units that have significantly changed compared to FIG. 3 are shown again.

FIG. 4 is a schematic representation of the multiple X-ray tube current profiles P1, P2 after collection of the first raw data and before adaptation of the second X-ray tube current profile P2. FIG. 4 shows in particular that in this example embodiment the first X-ray tube current duration P1D is adapted on the basis of a functional parameter of the patient during the collection of the first raw data.

FIG. 5 is a schematic representation of the multiple X-ray tube current profiles P1, P2 after adaptation of the second X-ray tube current profile P2. FIG. 5 shows in particular that in this example embodiment the second X-ray tube current amplitude P2A is adapted as a function of the at least one adapted X-ray tube current profile parameter, in particular as a function of the first X-ray tube current duration P1D.

Figure 6:
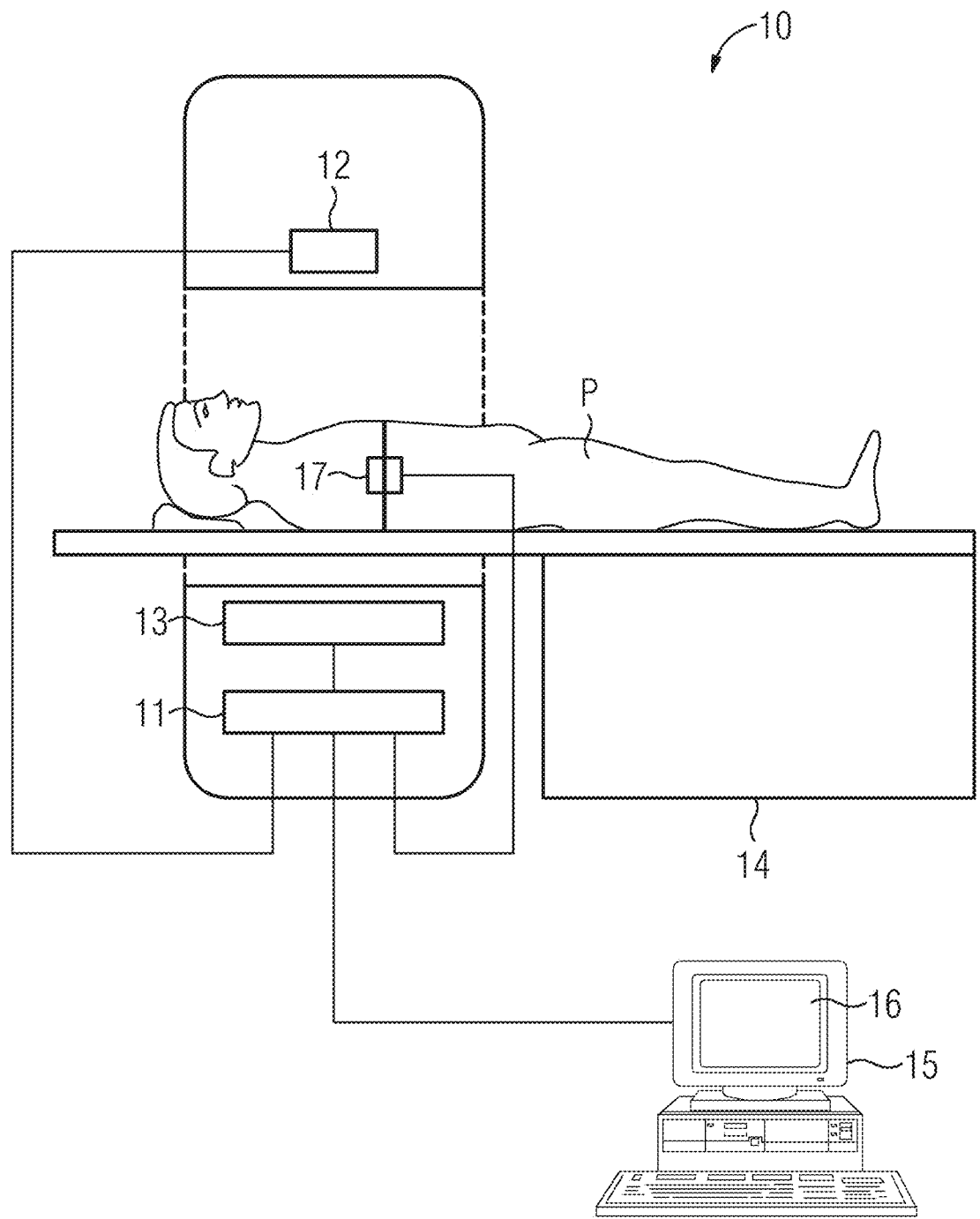

FIG. 6 shows a computed tomography system 10 that has a control unit 11 and an X-ray tube 12. The control unit 11 can be mapped in a processing unit of the computed tomography system 10. The computed tomography system is depicted in horizontal section in FIG. 6.

The X-ray tube 12 is configured to emit X-radiation in accordance with the multiple X-ray tube current profiles P1, P2. The computed tomography system 10 typically has an X-ray detector 13 that is configured to detect the X-radiation following penetration of the patient P, who is supported on an examination table 14. The computed tomography system 10 has a planning unit 15 with a display unit 16 and input unit. The medical image data set can preferably be provided on the display unit 16. In this case the medical image data set is thus preferably displayed to a user. The computed tomography system 10 has a functional patient monitoring unit 17, which in this example embodiment has a respiration belt.

Although the invention has been illustrated and described in detail by way of the preferred example embodiments, the invention is nevertheless not limited by the disclosed examples, and other variations can be derived therefrom by the person skilled in the art without departing from the scope of protection.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for provision of a medical image data set of a patient via an X-ray tube of a computed tomography system, the method comprising:

determining multiple X-ray tube current profiles of the X-ray tube in a control unit of the computed tomography system, wherein the multiple X-ray tube current profiles comprise a first X-ray tube current profile and a second X-ray tube current profile, form a measurement protocol for imaging measurement in the computed tomography system and satisfy a loading limit of the X-ray tube, while taking into consideration a functional reference parameter;

collecting, via the X-ray tube, first raw data of the patient according to the first X-ray tube current profile, wherein a functional parameter of the patient is recorded and wherein at least one X-ray tube current profile parameter of the first X-ray tube current profile is adapted during the collecting of the first raw data according to the functional parameter, to create at least one adapted X-ray tube current profile parameter;

adapting the second X-ray tube current profile in the control unit such that, as a function of the at least one adapted X-ray tube current profile parameter, the second X-ray tube current profile satisfies the loading limit of the X-ray tube, to create an adapted second X-ray tube current profile;

collecting, via the X-ray tube, second raw data of the patient according to the adapted second X-ray tube current profile;

reconstructing the medical image data set of the imaging measurement based upon the first raw data and the second raw data, to create a reconstructed medical image data set; and provisioning the reconstructed medical image data set.

2. The method of claim 1, wherein the functional parameter of the patient describes at least one of a respiration and a cardiac phase of the patient.

3. The method of claim 1, wherein the measurement protocol for the collecting of the first raw data and the measurement protocol for the collecting of the second raw data differ from one another in at least one of:
   a z-position of a measurement range of the measurement protocol, and
   in a phase within a period of a physiological function of the patient.

4. The method of claim 1, wherein the adapting of the second X-ray tube current profile is performed using an artificial neural network.

5. The method of claim 1, wherein the loading limit of the X-ray tube includes a temperature threshold of the X-ray tube.

6. The method of claim 1, wherein the at least one X-ray tube current profile parameter includes at least one of
   a first X-ray tube current amplitude, a first X-ray tube current duration and a first X-ray tube idle period.

7. The method of claim 1, wherein adapting of the second X-ray tube current profile comprises adapting at least one of
   a second X-ray tube current amplitude, a second X-ray tube current duration and a second X-ray tube idle period.

8. The method of claim 7, wherein a reduction in the second X-ray tube current profile occurs during adapting, as a function of an extension of the first X-ray tube current profile as a result of the functional parameter of the patient, in order to satisfy the loading limit of the X-ray tube.

9. The method of claim 8, wherein the second X-ray tube current amplitude is reduced.

10. The method of claim 8, wherein the second X-ray tube current duration is reduced.

11. The method of claim 1, wherein a lengthening of an X-ray tube idle time occurs as a function of an extension of the first X-ray tube current profile as a result of the functional parameter of the patient.

12. The method of claim 1, wherein an extension in the second X-ray tube current profile occurs during the adapting as a function of a reduction of the first X-ray tube current profile, as a result of the functional parameter of the patient.

13. The method of claim 12, wherein at least one of a second X-ray tube current amplitude and a second X-ray tube current duration are increased.

14. A computed tomography system, comprising:
   a control unit to determine multiple X-ray tube current profiles of an X-ray tube, wherein the multiple X-ray tube current profiles include a first X-ray tube current profile and a second X-ray tube current profile, form a measurement protocol for imaging measurement in the computed tomography system and satisfy a loading limit of the X-ray tube, while taking into consideration a functional reference parameter; and
   the X-ray tube configured to collect first raw data of a patient according to the first X-ray tube current profile, wherein a functional parameter of the patient is recorded and wherein at least one X-ray tube current profile parameter of the first X-ray tube current profile is adapted during collecting of the first raw data according to the functional parameter, to create at least one adapted X-ray tube current profile parameter,
   wherein the control unit is further configured to
      adapt the second X-ray tube current profile in the control unit such that, as a function of the at least one adapted X-ray tube current profile parameter, the second X-ray tube current profile satisfies the loading limit of the X-ray tube, to create an adapted second X-ray tube current profile, the X-ray tube being further configured to collect second raw data of the patient according to the adapted second X-ray tube current profile,
      reconstruct a medical image data set of the imaging measurement based upon the first raw data and the second raw data, to create a reconstructed medical image data set of the patient, and
      provision the reconstructed medical image data set of the patient.

15. A non-transitory computer readable medium storing a program that is directly loadable onto a memory of a processing unit, the program including program code segments to execute the method of claim 1 when the program is executed in the processing unit.

16. The method of claim 2, wherein the measurement protocol for the collecting of the first raw data and the measurement protocol for the collecting of the second raw data differ from one another in at least one of:
   a z-position of a measurement range of the measurement protocol, and
   in a phase within a period of a physiological function of the patient.

17. The method of claim 2, wherein the adapting of the second X-ray tube current profile is performed using an artificial neural network.

18. The method of claim 2, wherein the loading limit of the X-ray tube includes a temperature threshold of the X-ray tube.

19. The method of claim 2, wherein the at least one X-ray tube current profile parameter includes at least one of
   a first X-ray tube current amplitude, a first X-ray tube current duration and a first X-ray tube idle period.

20. The method of claim 2, wherein adapting of the second X-ray tube current profile comprises adapting at least one of
   a second X-ray tube current amplitude, a second X-ray tube current duration and a second X-ray tube idle period.

* * * * *